United States Patent [19]

Polans et al.

[11] Patent Number: 5,405,749

[45] Date of Patent: Apr. 11, 1995

[54] METHOD FOR IDENTIFYING AND PURIFYING A CANCER ASSOCIATED RETINOPATHY AUTOANTIGEN, AND TESTING PATIENT SERUM FOR THE AUTOANTIBODY TO THE AUTOANTIGEN

[76] Inventors: Arthur S. Polans, 3257 SE. Ankeny St., Portland, Oreg. 97214; Krzysztof Palczewski, 11850 SW. Blakeny St., Beaverton, both of Oreg. 97005

[21] Appl. No.: 804,894

[22] Filed: Dec. 6, 1991

[51] Int. Cl.$^6$ ................ G01N 33/574; C07K 3/00; C07K 13/00

[52] U.S. Cl. ................ 435/7.23; 435/7.2; 435/7.21; 435/7.92; 436/506; 436/813; 436/63; 436/64; 530/350; 530/413; 530/416; 530/417

[58] Field of Search ............ 435/7.23, 7.2, 7.21, 435/7.92; 436/506, 813, 63, 64, 541; 530/350, 403, 413, 416, 417

[56] References Cited

PUBLICATIONS

Dizhoor, A. M., et al, Science, vol. 251, 915–918, 22 Feb. 1991.

Kutuzov, M. A., et al, FEBS Letters, vol. 293, 21–24, Nov. 1991.

Dizhoor, A. M. et al. Biochem. Biophys. Res. Commun., vol. 162, 544–547, 1989.

Brain, L., and F. H. Norris: The Remote Effects of Cancer on the Nervous System. Grune & Stratton, New York, 1965.

Brain L., and M. Wilkinson: Subacute cerebellar degeneration associated with neoplasms. Brain. 88:465–478, 1965.

Brain W. R., P. M. Daniel, and J. G. Greenfield: Subacute cortical cerebellar degeneration and its relation to carcinoma. J. Neurol. Neurosurg. Psychiatr. 14:59–75, 1951.

Croft, P. B., and M. Wilkinson: Carcinomatous neuromyopathy: its incidence in patients with carcinoma of the lung and carcinoma of the breast. Lancet. :184–188. 1963.

Denny-Brown, D.: Primary sensory neuropathy with muscular changes associated with carcinoma. J. Neurol. Neurosurg. Psychiatr. 11:73–87, 1948.

Hawley, R. J., M. H. Cohen, N. Saini, and V. W. Armbrustmacher: The carcinomatous neuromyopathy of oat cell lung cancer. Ann. Neurol. 7:65–72, 1980.

Henson, R. A., and H. Urich: Cancer and the Nervous System: The Neurological Manifestations of Systemic Malignant Disease. Blackwell Scientific, Oxford. 346–367, 1982.

Bunn, P. A., and J. D. Minna Paraneoplastic syndromes. In Cancer: Principles and Practice of Oncology. V. T. Devita, S. A. Rosenberg, and S. Hellman, editors, J. B. Lippincott & Co., Philadelphia, 1797–1842, 1982.

Norris, F.: The remote effects of cancer on the nervous system. Z. Neurol. 201:201–207, 1972.

Sawyer, R. A., J. B. Selhorst, L. E. Zimmerman, and W. F. Hoyt: Blindness caused by photoreceptor degeneration as a remote effect of cancer. Am. J. Ophthalmol. 81:606–613, 1976.

Schold, S. C., E. S. Cho, and M. Somasundaram: Subacute motor neuronapathy: A remote effect of lymphoma. Ann. Neurol. 5:271–287, 1979.

(List continued on next page.)

*Primary Examiner*—Toni R. Scheiner
*Attorney, Agent, or Firm*—Kolisch, Hartwell, Dickinson, McCormack & Heuser

[57] ABSTRACT

A method of screening for cancer-associated retinopathy including the steps of acquiring a purified aliquot of 26 kDa protein, and, utilizing this protein, or peptides derived therefrom, performing a patient-serum assay to identify in a sample of a patient's serum the presence of autoantibodies to the 26 kDa protein autoantigen.

8 Claims, 3 Drawing Sheets

OTHER PUBLICATIONS

Anderson, N. E., M. K. Rosenblum, and J. B. Posner: Paraneoplastic cerebellar degeneration: clinical-immunologic correlations. Ann. Neurol. 24:559–567, 1988.

Keltner, J. L., A. M. Roth, and R. S. Chang: Photoreceptor degeneration: possible autoimmune disorder. Arch. Ophthalmol. 101:564–569, 1983.

Kornguth, S. E., R. Klein, R. Appen, and J. Choate: Occurrence of antiretinal ganglion cell antibodies in patients with small cell carcinoma of the lung. Cancer. 50:1289–1293, 1982.

DeAizpurua, H. J., E. H. Lambert, G. E. Greismann, B. M. Olivera, and V. A. Lennon: Antagonism of voltage-gated calcium channels in small cell carcinomas of patients with and without Lambert–Eaton myasthenic syndromes by autoantibodies, ω–conotoxin and adenosine. Cancer Res. 48:4719–4724, 1988.

Kim, Y. I., and E. Neher: IgG from pateints with Lambert–Eaton syndrome blocks voltage-dependent calcium channels. Science (Wash. D.C.). 239:405–408, 1988.

Newsom–Davis, J.: Lambert–Eaton myasthenic syndrome. Sem. Immunopathol. 8:129–140, 1985.

Furneaux, H. F., L. Reich, and J. B. Posner: Autoantibody synthesis in the central nervous system of patients with paraneoplastic syndromes. Neurology. 40:1085–1091, 1990.

Greenlee, J. E., and H. I. Lipton: Anti–cerebellar antibodies in serum and cerebrospinal fluid of a patient with oat cell carcinoma of the lung and paraneoplastic cerebellar degeneration. Ann. Neurol. 19:82–85, 1986.

Buchanan, T. A. S., T. A. Gardiner, and D. B. Archer: An ultrastructural study of retinal photoreceptor degeneration associated with bronchial carcinoma. Am. J. Ophthalmol. 97:277–287, 1984.

Grunwald, G. B., M. A. Simmonds, R. Klein, and J. E. Kornguth: Autoimmune basis for visual paraneoplastic syndrome in patients with small cell lung carcinoma. Lancet. i:658–661, 1985.

Thirkill, C. E., P. Fitzgerald, R. C. Sergott, A. M. Roth, N. K. Tyler, and J. L. Keltner: Cancer-associated retinopathy (CAR syndrome) with antibodies reacting with retino, optic–nerve and cancer cells. N. Engl. J. Med. 321:1589–1594, 1989.

Thirkill, C. E., A. M. Roth, and J. L. Keltner: Cancer–associated retinopathy. Arch. Ophthalmol. 105:372–375, 1987.

Tso, M. O. M.: Experiments on visual cells by nature and man: in search of treatment for photoreceptor degeneration. Invest. Ophthalmol. Vis. Sci. 30:2430–2460, 1989.

Galbraith, G. M. P., D. Emerson, H. H. Fudenberg, C. J. Gibbs, and D. C. Gajdusek: Antibodies to neurofilament protein in retinitis pigmentosa. J. Clin. Invest. 78:865–869, 1986.

Gurne, D., D. P. Edward, N. Mangini, and M. O. M. Tso: Antiretinal antibodies in serum of patients with age-related macular degeneration. Invest. Ophthalmol. Vis. Sci. 30:366a, 1989 Abstract only.

Papermaster, D. S.: Preparation of retinal rod outer segments. Methods Enzymol. 81:48–52, 1982.

Polans, A. S., J. Hermolin, and M. D. Bownds: Light-induced dephosphorylation of two proteins in frog rod outer segments. Influence of cyclic nucleotides and calcium. J. Gen. Physiol. 74:595–613, 1979.

Polans, A. S., and M. D. Burton: Sialoglycoproteins of the frog rod outer segment plasma membrane. Invest. Ophthalmol. Vis. Sci. 29:1523–1532, 1988.

Huang, J., and H. Matthews: Application of sodium dodecylsulfate-gel electrophoresis to low molecular weight polypeptides. Anal. Biochem. 188:114–117, 1990.

Schägger, H., and G. von Jagow: Tricine–sodium dodecylsulfatepolyacrylamide gel electrophoresis for the separation of proteins in the range of 1–100kDa. Anal. Biochem. 166:368–379, 1987.

Bradford, M.: A rapid and sensitive method for quantitation of microgram quantities of protein utilizing the principle of dye–binding. Anal. Bio–chem. 72:248–254, 1976.

Burton, M. D., L. T. Onstott, and A. S. Polans: The use of gold reagents to quantitate antibodies eluted from nitrocellulose blots: application to EM immunocytochemistry. Anal. Biochem. 183:225–230, 1989.

Wilden, U., and H. Kühn: Light–dependent phosphorylation of rhodopsin number of phosphorylation sites. Biochemistry. 21:3014–3022, 1982.

Crestfield, A. M., S. Moore, and W. J. Stein: The preparation and enzymatic hydrolysis of reduced and S-carboxymethylated proteins. J. Biol. Chem. 238:662–627, 1963.

Lai, C. H.: Studies on the structure of rabbit muscle aldolase. I. Cleavage with cyanogen bromide: an approach on the determination of the total primary structure. Arch. Biochem. Biophys. 128:202–211, 1968.

(List continued on next page.)

OTHER PUBLICATIONS

Matsudaira, P.: Sequence from picomole quantities of proteins electroblotted onto polyvinylidene difluoride membranes. J. Biol. Chem. 262:10035–10038, 1987.

Crabb, J. W., L. G. Armes, S. A. Carr, C. M. Johnson, G. D. Roberts, R. S. Bordoli, and W. L. McKeehan: Complete primary structure of prostatropin, a prostate epithelial cell growth factor. Biochemistry. 25:4988–4993, 1986.

West, K. W., and J. W. Crabb: Current Research in Protein Chemistry. J. J. Villafranca, editor. 37–48, 1990.

Crabb, J. W., C. M. Johnson, S. A. Carr, L. G. Armes, and J. C. Saari: The complete primary structure of the cellular retinaldehyde-binding protein from bovine retina. J. Biol. Chem. 263:18678–18687, 1988.

Polans, Arthur S., Janina Buczylko, John Carbb, and Krzysztof Palczewski: A photoreceptor calcium binding protein is recognized by autoantibodies obtained from patients with cancer-associated retinopathy. J. Cell Biol. 112:981–989, 1991.

```
                5              10             15             20             25             30
                |              |              |              |              |              |
  1 M G N S K S G A L S K E I L E E L Q L N T K F T E E E L S S
 31 W Y Q S F L K E C P S G R I T R Q E F Q T I Y S K F F P E A
 61 D P K A Y A Q H V F R S F D A N S D G T L D F K E Y V I A L
 91 H M T S A G K T N Q K L E W A F S L Y D V D G N G T I S K N
121 E V L E I V T A I F K M I S P E D T K H L P E D E N T P E K
151 R A E K I W G F F G K K D D D K L T E K E F I E G T L A N K
181 E I L R L I Q F E P Q K V K E K L K E K K L
```

Number of residues : 202.

Figure 2

|   | 1 | 2 | 3 | 4 |
|---|---|---|---|---|
| A. | .341 | .652 | 1.165 | 1.324 |
| B. | .045 | .053 | .043 | .062 |
| C. | .048 | .052 | .053 | .053 |

METHOD FOR IDENTIFYING AND PURIFYING A CANCER ASSOCIATED RETINOPATHY AUTOANTIGEN, AND TESTING PATIENT SERUM FOR THE AUTOANTIBODY TO THE AUTOANTIGEN

BACKGROUND PUBLICATIONS

The following publications are referred to by corresponding number in this application, and their contents are hereby incorporated by reference into this disclosure as background information:

1. Brain, L., and F. H. Norris: The Remote Effects of Cancer on the Nervous System. Grune & Stratton, New York. 24, 1965.
2. Brain L., and M. Wilkinson: Subacute cerebellar degeneration associated with neoplasms. Brain. 88:465–478, 1965.
3. Brain W. R., P. M. Daniel, and J. G. Greenfield: Subacute cortical cerebellar degeneration and its relation to carcinoma. J. Neurol. Neurosurg. Psychiatr. 14:59–75, 1951.
4. Croft, P. B., and M. Wilkinson: Carcinomatous neuromyopathy: its incidence in patients with carcinoma of the lung and carcinoma of the breast. Lancet. i:184–188, 1963.
5. Denny-Brown, D.: Primary sensory neuropathy with muscular changes associated with carcinoma. J. Neurol. Neurosurg. Psychiatr. 11:73–87, 1948.
6. Hawley, R. J., M. H. Cohen, N. Saini, and V. W. Armbrustmacher: The carcinomatous neuromyopathy of oat cell lung cancer. Ann. Neurol. 7:65–72, 1980.
7. Henson, R. A., and H. Urich: Cancer and the Nervous System: The Neurological Manifestations of Systemic Malignant Disease. Blackwell Scientific, Oxford. 346–367, 1982.
8. Minna, J. D., and P. A. Bunn: Paraneoplastic syndromes. In Cancer: Principles and Practice of Oncology. V. T. Devita, S. A. Rosenberg, and S. Hellman, editors, J. B. Lippincott & Co., Philadelphia. 1476–1517, 1982.
9. Norris, F.: The remote effects of cancer on the nervous system. Z. Neurol. 201:201–210, 1972.
10. Sawyer, R. A., J. B. Selhorst, L. E. Zimmerman, and W. F. Hoyt: Blindness caused by photoreceptor degeneration as a remote effect of cancer. Am. J. Ophthalmol. 81:606–613, 1976.
11. Schold, S. C., E. S. Cho, and M. Somasundaram: Subacute motor neuronapathy: A remote effect of lymphoma. Ann. Neurol. 5:271–287, 1979.
12. Anderson, N. E., M. K. Rosenblum, and J. B. Posner: Paraneoplastic cerebellar degeneration: clinical-immunologic correlations. Ann. Neurol. 24:559–567, 1988.
13. Keltner, J. L., A. M. Roth, and R. S. Chang: Photoreceptor degeneration: possible autoimmune disorder. Arch. Ophthalmol. 101:564–569, 1983.
14. Kornguth, S. E., R. Klein, R. Appen, and J. Choate: Occurrence of antiretinal ganglion cell antibodies in patients with small cell carcinoma of the lung. Cancer. 50:1289–1293, 1982.
15. DeAizpurua, H. J., E. H. Lambert, G. E. Greismann, B. M. Olivera, and V. A. Lennon: Antagonism of voltage-gated calcium channels in small cell carcinomas of patients with and without Lambert-Eaton myasthenic syndromes by autoantibodies, w-conotoxin and adenosine. Cancer Res. 48:4719–4724, 1988.
16. Kim, Y. I., and E. Neher: IgG from patients with Lambert-Eaton syndrome blocks voltage-dependent calcium channels. Science (Wash. D.C.). 239:405–408, 1988.
17. Newsom-Davis, J.: Lambert-Eaton myasthenic syndrome. Sem. Immunopathol. 8:129–140, 1985.
18. Furneaux, H. F., L. Reich, and J. B. Posner: Autoantibody synthesis in the central nervous system of patients with paraneoplastic syndromes. Neurology. 40:1085–1091, 1990.
19. Greenlee, J. E., and H. I. Lipton: Anti-cerebellar antibodies in serum and cerebrospinal fluid of a patient with oat cell carcinoma of the lung and paraneoplastic cerebellar degeneration. Ann. Neurol. 19:82–85, 1986.
20. Buchanan, T. A. S., T. A. Gardiner, and D. B. Archer: An ultrastructural study of retinal photoreceptor degeneration associated with bronchial carcinoma. Am. J. Ophthalmol. 97:277–287, 1984.
21. Grunwald, G. B., M. A. Simmonds, R. Klein, and J. E. Kornguth: Autoimmune basis for visual paraneoplastic syndrome in patients with small cell lung carcinoma. Lancet. i:658–661, 1985.
22. Thirkill, C. E., P. Fitzgerald, R. C. Sergott, A. M. Roth, N. K. Tyler, and J. L. Keltner: Cancer-associated retinopathy (CAR syndrome) with antibodies reacting with retino, optic-nerve and cancer cells. N. Engl. J. Med. 321:1589–1594, 1989.
23. Thirkill, C. E., A. M. Roth, and J. L. Keltner: Cancer-associated retinopathy. Arch. Ophthalmol. 105:372–375, 1987.
24. Tso, M. O. M.: Experiments on visual cells by nature and man: in search of treatment for photoreceptor degeneration. Invest. Ophthalmol. Vis. Sci. 30:2430–2460, 1989.
25. Galbraith, G. M. P., D. Emerson, H. H. Fudenberg, C. J. Gibbs, and D. C. Gajdusek: Antibodies to neurofilament protein in retinitis pigmentosa. J. Clin. Invest. 78:865–869, 1986.
26. Gurne, D., D. P. Edward, N. Mangini, and M. O. M. Tso: Antiretinal antibodies in serum of patients with age-related macular degeneration. Invest. Ophthalmol. Vis. Sci. 30:366a, 1989.
27. Papermaster, D. S.: Preparation of retinal rod outer segments. Methods Enzymol. 81:48–52, 1982.
28. Polans, A. S., J. Hermolin, and M. D. Bownds: Light-induced dephosphorylation of two proteins in frog rod outer segments. Influence of cyclic nucleotides and calcium. J. Gen. Physiol. 74:595–613, 1979.
29. Polans, A. S., and M. D. Burton: Sialoglycoproteins of the frog rod outer segment plasma membrane. Invest. Ophthalmol. Vis. Sci. 29:1523–1532, 1988.
30. Huang, J., and H. Matthews: Application of sodium dodecylsulfate-gel electrophoresis to low molecular weight polypeptides. Anal. Biochem. 188:114–117, 1990.
31. Schagger, H., and G. von Jagow: Tricine-sodium dodecylsulfatepolyacrylamide gel electrophoresis for the separation of proteins in the range of 1–100 kDa. Anal. Biochem. 166:368–379, 1987.
32. Bradford, M.: A rapid and sensitive method for quantitation of microgram quantities of protein utilizing the principle of dye-binding. Anal. Bio-chem. 72:248–254, 1976.
33. Burton, M.D., L. T. Onstott, and A. S. Polans: The use of gold reagents to quantitate antibodies eluted 33. from nitrocellulose blots: application to EM immunocytochemistry. Anal. Biochem. 183:225–230, 1989.
34. Wilden, U., and H. Kühn: Light-dependent phosphorylation of rhodopsin number of phosphorylation sites. Biochemistry. 21:3014–3022, 1982.
35. Crestfield, A. M., S. Moore, and W. J. Stein: The preparation and enzymatic hydrolysis of reduced and S-carboxymethylated proteins. J. Biol. Chem. 238:622–627, 1963.
36. Lai, C. H.: Studies on the structure of rabbit muscle aldolase. I. Cleavage with cyanogen bromide: an approach on the determination of the total primary structure. Arch. Biochem. Biophys. 128:202–211, 1968.
37. Matsudaira, P.: Sequence from picomole quantities of proteins electroblotted onto polyvinylidene difluoride membranes. J. Biol. Chem. 262:10035–10038, 1987.
38. Crabb, J. W., L. G. Armes, S. A. Carr, C. M. Johnson, G. D. Roberts, R. S. Bordoli, and W. L. McKeehan: Complete primary structure of prostatropin, a prostate epithelial cell growth factor. Biochemistry. 25:4988–4993, 1986.
39. West, K. A., and J. W. Crabb: Current Research in Protein Chemistry. J. J. Villafranca, editor. 37–48, 1990.
40. Crabb, J. W., C. M. Johnson, S. A. Carr, L. G. Armes, and J. C. Saari: The complete primary structure of the cellular retinaldehyde-binding protein from bovine retina. J. Biol. Chem. 263:18678–18687, 1988.
41. Polans, Arthur S., Janina Buczylko, John Crabb, and Krzysztof Palczewski: A photoreceptor calcium binding protein is recognized by autoantibodies obtained from patients with cancer-associated retinopathy. J. Cell Biol. 112:981–989.

Background of the Invention

The present invention relates to diagnosis of cancer-associated retinopathy, and additionally, and in this context, to a method for identifying and purifying a cancer-associated retinopathy autoantigen, and performing patient-serum assays using the purified autoantigen to identify in a patient's serum the presence of autoantibodies to the autoantigen.

Various neurodegenerative diseases are known to be associated with different types of cancer, even though the tumor and its metastases have not invaded the nervous system (1, 2, 3, 4 5, 6, 7, 8, and 9). These "remote effects" of cancer, or paraneoplastic syndromes, are of undetermined etiology, although some studies have implicated viral, hormonal or toxic origins (1, 6, 10, and 11). Alternatively, others have thought that these degenerative diseases may stem from an autoimmune response which is directed towards antigens or epitopes found in both the tumor and specific neurons (12, 13, and 14). Evidence supporting this connection has been presented in the case of Eaton-Lambert myasthenic syndrome, a disease of the peripheral nervous system, in which the binding of autoantibodies at the neuromuscular junction interferes with the calcium-induced release of neurotransmitter (15, 16, and 17). An autoimmune component also has been suggested in several diseases of the central nervous system, including paraneoplastic cerebellar degeneration (12, 18, and 19) and cancer-associated retinopathy (20, 21, 13, 14, 22, and 23).

With cancer-associated retinopathy ("CAR") retinal degeneration often precedes diagnosis of the tumor, and loss of vision may occur rapidly. Like other retinal degenerations, CAR spares the inner retina while causing photoreceptors to degenerate (20 and 13). However, during CAR there is no evidence of pigment migration or epiretinal membrane formation, as occurs in retinitis pigmentosa, nor are the vasculature or optic nerve head damaged (20). The inflammatory response characteristic of uveitis is not associated with CAR. Despite these differences, autoantibodies may be involved in all of these degenerative diseases of the retina (24). Retinal antigens of 58–62 kDa, 145 kDa and 205 kDa have been observed to bind antisera obtained from patients with retinitis pigmentosa and age-related macular degeneration (25 and 26). An earlier study of CAR also identified a retinal antigen of 65 kDa, as well as a low molecular weight protein of approximately 20 kDa (21). More recent and extensive studies of CAR have focused on a prominent retinal antigen of approximately 23 kDa (12, 22, and 23). Several of these antisera cross-react with the 68 kDa neurofilament protein, and this finding has led to the speculation that autoantibodies associated with retinal degenerations may be directed towards cytoskeletal elements found in the tumor and retinal cells (21 and 26).

The results obtained from immunohistochemical studies using CAR antisera have been inconsistent; different populations of retinal cells have been labeled by different CAR antisera (13, 14, and 22). However, antibodies from these complex human sera were not affinity-purified, therefore, it was difficult to associate a specific antibody with a particular labeling pattern. Nor were EM-immunocytochemical studies performed. For these reasons, the identity of the retinal antigen that binds the CAR autoantibodies and its precise localization remained uncertain. The functional identification of the CAR antigen also had not been ascertained.

Presently, there is no laboratory test which can conclusively diagnose CAR. A positive test for the presence of CAR autoantibodies would aid in the diagnosis of the retinal disease and enable the physician to treat effectively the patient and prevent or delay further vision loss. Moreover, since the neurological symptoms often occur prior to the diagnosis of cancer, a positive antibody response may act as an early warning for cancer in these patients.

Therefore, a general object of the present invention is to provide a laboratory method and diagnostic test for diagnosing cancer-associated retinopathy.

Another object of the invention is to provide a novel method which utilizes a purified cancer-associated retinopathy autoantigen in a patient-serum assay to detect the presence of cancer-associated retinopathy autoantibodies.

Still another object is to provide a method for identifying and purifying a cancer-associated retinopathy autoantigen.

Given the above background, the present invention proposes a novel method for diagnosing cancer-associated retinopathy employing the fundamental steps of acquiring a purified aliquot of 26 kDa protein (SEQ ID No: 1) and, utilizing selectively either the protein or peptides derived therefrom, performing a patient-serum assay to identify in a sample of a patient's serum the presence of autoantibodies to 26 kDa protein autoantigen. Acquisition of such an aliquot can occur, for example, through a purification procedure proposed herein as a feature of this invention, through production (via synthesizing) of protein fragments, or through a production of recombinant 26 kDa protein.

In accordance with one way of viewing a preferred method of practicing the invention, such practice includes the steps of identifying as a cancer-associated retinopathy herald a 26 kDa protein autoantigen, acquiring from a selected retina source and purifying from the source an aliquot of 26 kDa protein, and performing a patient-serum assay utilizing such 26 kDa protein to identify autoantibodies in the patient's serum to the 26 kDa protein.

These and other objects and features of the present invention will become more fully apparent when the following detailed description of a preferred embodiment is read in connection with the accompanying drawings, wherein:

FIG. 1 shows the SDS-PAGE electrophoresis staining pattern of purified CAR antigen;

FIG. 2 shows the amino acid sequence of the 26 kDa CAR antigen (SEQ ID NO:1). The single letter code for amino acids is used (Eur. J. Biochem. 1968, 5:151-153);

FIG. 3a illustrates, in rows A, B and C for each of three different patients—CAR patient, NORMAL patient and NON-CAR RETINOPATHY patient, respectively—the visually observable binding reactions of respective dilution series for the three patients.

FIG. 3b, in rows A, B and C, presents quantified spectrophotometric data associated with the reactions pictured in FIG. 3a.

DETAILED DESCRIPTION AND BEST MODE FOR CARRYING OUT THE INVENTION

Figure 1:
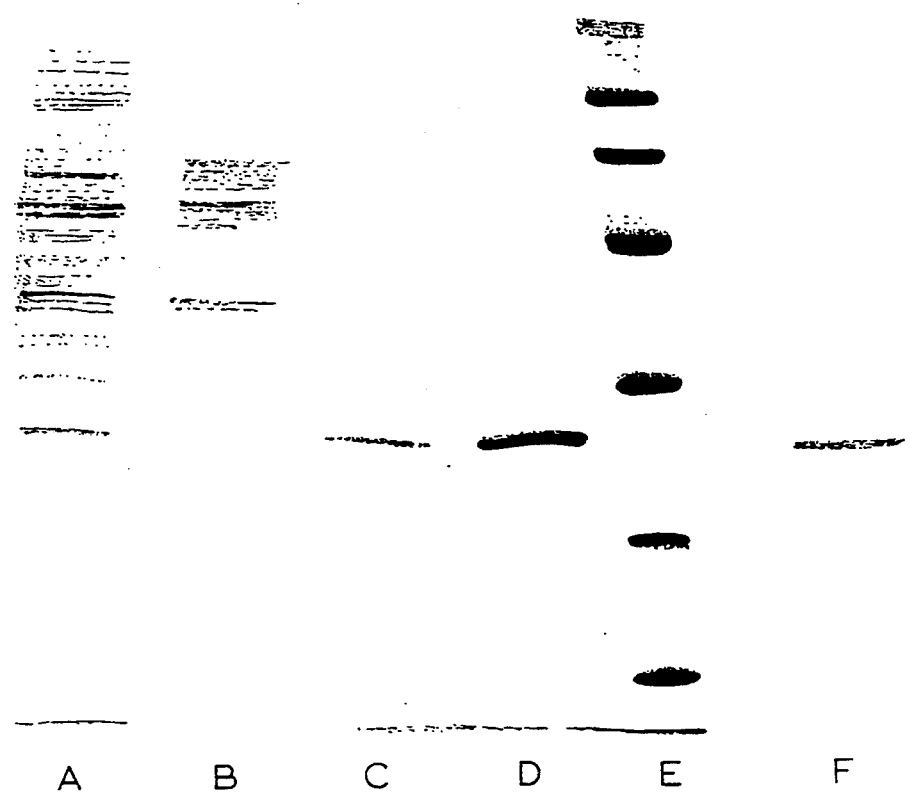

Using the sera from five individuals, applicants have identified a 26 kDa CAR autoantigen (SEQ ID NO: 1) that is localized with highest density to the cell bodies of the retinal rods and cones but also is found in the inner and outer segments of both types of photoreceptors. Further, applicants have purified the 26 kDa CAR autoantigen to homogeneity using a convenient, two-step chromatographic procedure. Cleavage products of the purified protein were used to determine the amino acid sequence of the protein, which was identified as a member of a family of calcium binding proteins. Using either the purified (derived) protein, or synthetic peptides derived from the known sequence of the protein, applicants can test the serum from patients suspected of having CAR and related diseases for the presence of autoantibodies.

In order to identify and, then, to purify the autoantigen associated with cancer-associated retinopathy, it is first necessary to affinity-purify autoantibodies present in CAR antisera. Therefore, in this detailed description, applicants will initially describe the affinity-purification of antibodies from CAR antisera, and the use of these antibodies in parallel Western blot analyses and EM-immunocytochemical studies.

Preparation of Human Rod Outer Segments

Rod outer segments (ROS) were isolated from human retinas according to the procedures developed for bovine ROS, as described by Papermaster (27). In other experiments, human retinas were disrupted using a Teflon pestle and solubilized with 0.15% wt/vol deoxycholate. After centrifugation at 100,000g (SW28; Beckman Instruments, Fullerton, Calif.), the supernatant and previously isolated ROS were processed for SDS-PAGE.

All isolations were done in the presence of protease inhibitors: 2 μg/ml leupeptin, 4 μg/ml PMSF, and 10 μg/ml aprotinin.

SDS-PAGE and Western Blot Analysis

Treatment of protein samples is described in detail elsewhere (28), as are the procedures for electrophoresis and transfer of protein to nitrocellulose (29). In some experiments, Immobilon ™ (Millipore Corp., Bedford, Mass.) was used in place of nitrocellulose. Separation of peptide fragments was accomplished with a Tricine-SDS-gel electrophoresis system (30 and 31) using a 16% polyacrylamide gel. Protein determinations were made with a dye binding assay (32).

Western blots were rinsed twice in Tris.NaCl and nonspecific sites were saturated by incubation for 45 minutes at 37° C. with a solution of Tris.NaCl containing 5% wt/vol BSA. The membrane then was incubated for 1-2 hours either with CAR antisera at a dilution of 1:500 or affinity-purified antibody (see below). All incubations were performed in 0.1% BSA-TrisoNaCl. Blots were rinsed six times each for 5 minutes with 0.1% BSA-Tris.NaCl and then incubated for 2 hours with a 1:50 dilution of goat anti-human IgG gold conjugate in 0.1% BSA-Tris.NaCl containing 0.4% wt/vol gelatin. After four rinses with 0.1% BSA-Tris.-NaCl blots were rinsed with water (twice for 30 seconds each) and silver-enhanced 10-15 minutes according to the manufacturer's procedures.

Affinity-Purification of CAR Antibodies

Procedures for the affinity-purification of complex antisera have been published in detail elsewhere (33). Briefly, blots of human ROS protein were incubated with CAR antiserum. A single lane from the blot was stained using gold conjugates and silver enhancement as described above. The stained lane was realigned with the blot, and protein bands corresponding to the sites of antibody staining were excised separately. Antibody was eluted from excised bands using glycine.HCl pH 2.2, followed by neutralization with Tris base. The antibody eluate was quantitated for human IgG using an immunogold procedure (33). After concentrating the eluate in a Centricon 30 tube (Amicon Corp., Danvers, Mass.), the sample was mixed with a further solution to yield 0.1% BSA, 0.1% normal goat serum in either Tris.NaCl or PBS. In this manner, we have demonstrated that only autobodies to 26 kDa protein found in retina correlated with CAR (41).

Purification of the 26 kDa CAR Antigen (SEQ ID NO:1)

ROS from 150 bovine retinas was prepared as described previously (34) and finally resuspended in 20 ml of 50 mM Hepes buffer, pH 7.5, containing 1.0 mM EDTA and 100 mM NaCl. The suspension was homogenized with a glass-glass tissue homogenizer and centrifuged at 48,000g (J 20.1; Beckman Instruments) for 10 minutes. The supernatant was collected and the extraction procedure was repeated three times. These steps were conducted at 4° C. under dim red illumination. Calcium chloride then was added to the combined supernatants in order to yield a final concentration of 2 mM.

A Phenyl-Sepharose column (1.0×4.0 cm) was prepared and equilibrated with 50 mMHepes buffer, pH 7.5 containing 2 mM $CaCl_2$ and 100 mM NaCl. The bovine ROS extract was applied to the column and the column was washed with equilibrating buffer at a rate of 15 ml/h until the $A_{280}$ nm returned to the baseline. Bound material was eluted with 50 mM Hepes buffer, pH 7.5, containing 10 mM EDTA and 100 mM NaCl at a rate of 5 ml/h. 1 ml fractions were collected, and aliquots were subjected to SDS-PAGE and Western blot analysis using CAR antiserum.

Fractions containing the 26 kDa CAR antigen were combined and dialyzed against 1 liter of 10 mM bis [2-hydroxymethyl] iminotris [hydroxymethyl]-methane (BTP) buffer, pH 8.4. Aliquots containing 0.5–1.0 mg of protein were applied to Mono Q column (Polystyrene divinybenzene resin, HR 5×50 mm; Pharmacia Fine Chemicals, Piscataway, N.J.) equilibrated with 10mM BTP buffer, pH 8.4. The column was developed with a linear gradient of NaCl (0–0.25M) during 20 minutes at a rate of 0.5 ml/min. 0.5 ml fractions were collected, and aliquots were analyzed by SDS-PAGE and Western blot analysis using CAR antiserum. The 26 kDa CAR antigen eluted at ~100 mMNaCl.

As seen in FIG. 1, bovine rod outer segments were extracted with EDTA, and the soluble fraction (after adjusting the calcium concentration) was applied to a Phenyl-Sepharose column. An aliquot of the soluble extract was separated by SDS-PAGE, and the protein staining pattern is shown in lane A. Protein which did not bind to the column is shown in lane B, whereas bound material which could be eluted with EDTA is stained in lane C. The 26 kDa CAR protein represented the majority of protein which was bound to the column. The eluted material depicted in lane C was further purified by Mono Q chromatography, and an aliquot of the final sample is shown in lane D. Molecular weight standards in lane E were: phosphorylase b (94 kDa), bovine serum albumin (67 kDa), ovalbumin (43 kDa), carbonic anhydrase (30 kDa), soybean trypsin inhibitor (20 kDa), and alpha-lactalbumin (14 kDa). An immunoblot of the purified fraction shown in lane D was prepared according to the procedures essentially described by Towbin et al., 1979. CAR staining of the immunoblot is shown in lane F demonstrating that the purified 26 kDa protein is the immunoreactive antigen recognized by CAR antisera.

The purified protein can be used as a substrate for ELISA (as described below), or synthetic peptides derived from the known sequence of the 26 kDa protein (see FIG. 2) can serve as substrate in the assay.

Amino Acid Sequence Analysis

The purified 26 kDa CAR protein (SEQ ID NO:1) was lyophilized and S-carboxymethylation was performed following the methods described by Crestfield et al. (35). Cyanogen bromide (CNBr) cleavage of the S-carboxymethylated protein was performed over a 72-hour period according to the methods published by Lai (36). CNBr peptide fragments were separated by Tricine-SDS-gel electrophoresis (30 and 31) and electroblotted to Immobilon (Millipore Corp.) for sequence and amino acid analysis (37). Additionally, the purified 26 kDa protein was subjected to cleavage at lysyl residues with endoproteinase Lys-C (Boehringer-Mannheim Biochemicals, Indianapolis, Ind.), and peptides were isolated by narrowbone RP-HPLC (Vydac, Hesperia, Calif.) using the Applied Biosystems model 130 system (Applied Biosystems, Inc., Foster City, Calif.) (38).

Phenylthiocarbamyl amino acid analysis was performed according to West and Crabb (39) using an Applied Biosystems automatic system (models 420/130/920). HCl vapor phase hydrolysis was performed at 150° C. for 1 hour. Automatic Edman degradations were performed as previously described (40) with an Applied Biosystems gas phase sequencer (model 470) and an on-line Phenylthiohydantoin amino acid analyzer (model 120) using the 03RPTH sequencer program and the manufacturer's recommended program and solvents for the PTH analyzer.

FIG. 2 illustrates the known sequence of the purified 26 kDa protein/CAR autoantigen. The single letter code for amino acids is used (Eur. J. Biochem, 1968, 5:151–153).

Enzyme Linked Immunosorbent Assay

Purified 26 kDa protein (SEQ ID NO: 1) is adsorbed to polystyrene 96-well microtiter plates (Corning Glass Works, Corny, N.Y.) by incubation overnight in Tris buffer, pH 9.0. Additional vacant sites on the plates are blocked by incubation with 1% w/v BSA for 1 hr. at room temperature. After washing the plates with 0.1% w/v BSA, serum obtained from patients is serially diluted from 1/100 to 1/2,500 and a total volume of 100 $\mu$l is added to the wells. A second set of wells is incubated with normal human serum which serves as a control. Incubation is conducted at room temperature for 1 hour. After thorough washing, 100 $\mu$l of a commercially-available secondary antibody (goat anti-human IgG) conjugated with horseradish peroxidase (Vector Laboratories, Burlingame, Calif.) is added to the wells at 1 $\mu$g/ml, for a 30-min. incubation. Alternatively, for greater sensitivity, the detection system can consist of incubations with 100 $\mu$l of a 1 $\mu$g/ml solution of biotinyl goat anti-human IgG (Vector Laboratories) followed by streptavidin-horseradish peroxidase complex (Amersham Corp., Arlington Heights, Ill.) at the same concentration. (Other enzyme-linked secondary antibodies, i.e., alkaline phosphatase, also can be used for detection.) The commercially-available substrate 3,3', 5 5'-tetramethylbenzidine (TMB) (Biorad Laboratories, Richmond, Calif.), in the presence of hydrogen peroxide, is then added according to the manufacturer's directions, to visualize antibody binding. The reaction can be visually inspected or quantified using a plate reader. The patient's serum is compared to the control consisting of normal human serum.

Alternatively, synthetic peptides derived from the 26 kDa protein can be conjugated to a carrier molecule, i.e., BSA, and adsorbed to microtiter wells for the enzyme-linked immunosorbent assay ("ELISA"), as just described.

Figures 3A, 3B:
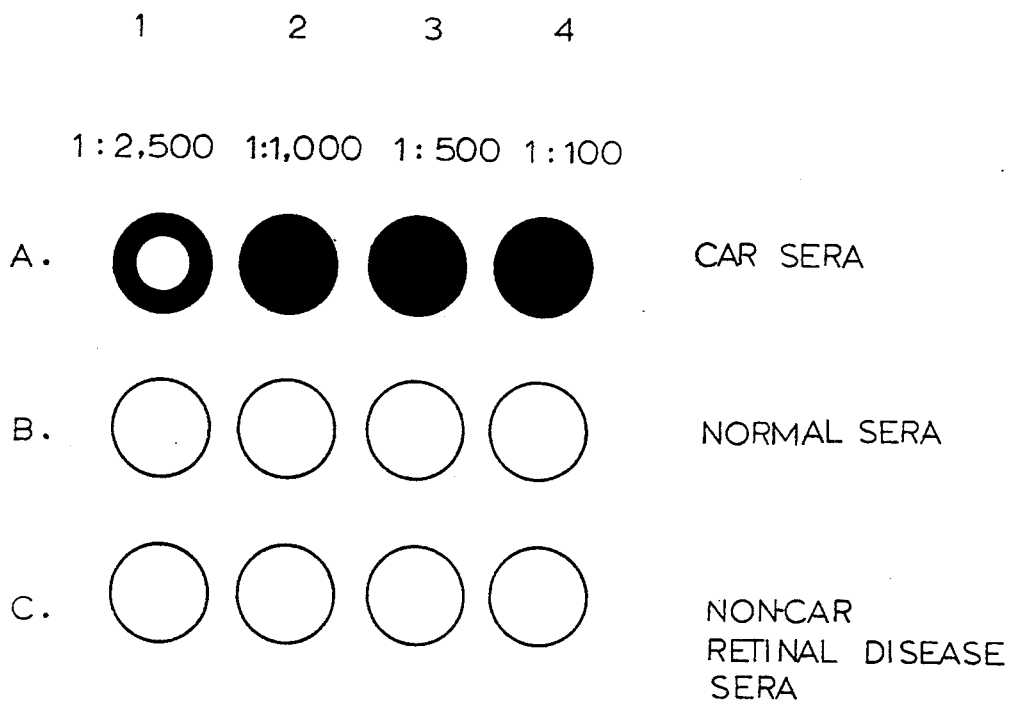

FIG. 3a illustrates the binding of a CAR serum sample to wells of a microtiter plate that have been coated with purified 26 kDa protein. The microtiter plate can be visually inspected for dark reaction product indicative of a positive binding response, as in FIG. 3a, or such antibody binding can be quantified spectrophotometrically using a microtiter plate reader (Biorad Laboratories) as shown in FIG. 3b. FIGS. 3a and 3b illustrate two controls. Both normal human serum and the serum from a patient with a retinal disorder other than CAR do not bind to the microtiter wells coated with the 26 kDa CAR protein. Thus, antibody binding correlates precisely with CAR. (As demonstrated in our publication, Polans et al., 1991, patients with retinal degenerations other than CAR do not display autoantibodies to the 26 kDA protein. Patients with similar cancers as the CAR patients but who do not have an associated retinopathy also do not have autoantibodies to the 26 kDa protein. Finally, individuals with other autoimmune disorders, such as Guillain Barre and Lupus, also do not have autoantibodies to the 26 kDa protein.)

In summary, applicants have affinity-purified the autoantibodies from complex CAR sera to identify the principal, if not sole, retinal antigen as a 26 kDa protein. In EM immunocytochemical experiments, applicants localized the 26 kDa protein to the cell bodies, inner and outer segments of both rods and cones. Applicants purified the rod protein by a two-step chromatographic procedure and developed a laboratory method and diagnostic test for identifying the presence of CAR autoantibodies in a patient's serum by using applicants' purified autoantigen.

Owing to the characterization of the 26kDa protein, it is also now possible to examine biopsy tissue obtained from CAR patients and look for the expression of an immunoreactive calcium-binding protein or shared determinant.

While a preferred embodiment of the invention has been described, it should be appreciated that variations and modifications may be made without departing from the scope of the invention as defined by the claims.

---

It is desired to claim and secure by Letters Patent:

1. A method for detecting autoantibodies indicative of cancer-associated retinopathy, wherein the method comprises
   (a) acquiring a selected retina source, and purifying therefrom an aliquot of a purified and isolated protein according to SEQ ID NO:1, wherein the step of purifying includes a two-step chromatographic procedure,
   (b) performing an immunoassay by contacting a patient's serum with the isolated protein of step (a) and detecting in the patient's serum the presence of autoantibodies which specifically bind the isolated protein,
   wherein the presence of autoantibodies which specifically bind the isolated protein is indicative of cancer-associated retinopathy.

2. The method of claim 1, wherein the immunoassay is an enzyme-linked immunosorbent assay.

3. The method of claim 1, wherein the isolated protein is purified from rod outer segments of human or bovine retinas.

4. The method of claim 1, wherein the step of purifying includes the steps of (1) introducing an extract of the retina source onto a first chromatographic column which binds the protein, (2) eluting the bound fraction containing the protein from the first column to form a first eluate, and (3) applying the first eluate to a second chromatographic column which binds the protein to obtain a second eluate containing the purified protein.

5. The method of claim 4, wherein the first chromatographic column is a Phenyl-Sepharose column and the second chromatographic column is a Mono Q column.

6. A method for purifying a retinal protein which comprises the steps of
   providing an extract from a retinal source, and
   deriving from such extract a purified and isolated protein according to SEQ ID NO:1 by a two-step chromatographic procedure.

7. A method for detecting autoantibodies indicative of cancer-associated retinopathy (CAR) comprising:
   providing an aliquot of a purified and isolated protein of about 26 kDa or a peptide derived therefrom which is specifically bound by purified CAR antibodies;
   contacting the purified protein with a serum sample from a patient;
   detecting binding between the purified protein and CAR antibodies from the patient's serum, thereby determining whether the patient has autoantibodies indicative of CAR.

8. The method of claim 7 wherein the protein has an amino acid sequence according to SEQ ID NO:1.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 202 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
( A ) ORGANISM: 26KDa retinal antigen ( x i ) SEQUENCE DESCRIPTION: SEQ ID NO:1:

```
Met Gly Asn Ser Lys Ser Gly Ala Leu Ser Lys Glu Ile Leu Glu Glu
 1               5                  10                  15

Leu Gln Leu Asn Thr Lys Phe Thr Glu Glu Glu Leu Ser Ser Trp Tyr
             20                  25                  30

Gln Ser Phe Leu Lys Glu Cys Pro Ser Gly Arg Ile Thr Arg Gln Glu
         35                  40                  45

Phe Gln Thr Ile Tyr Ser Lys Phe Phe Pro Glu Ala Asp Pro Lys Ala
     50                  55                  60

Tyr Ala Gln His Val Phe Arg Ser Phe Asp Ala Asn Ser Asp Gly Thr
 65                  70                  75                  80

Leu Asp Phe Lys Glu Tyr Val Ile Ala Leu His Met Thr Ser Ala Gly
                 85                  90                  95

Lys Thr Asn Gln Lys Leu Glu Trp Ala Phe Ser Leu Tyr Asp Val Asp
                100                 105                 110

Gly Asn Gly Thr Ile Ser Lys Asn Glu Val Leu Glu Ile Val Thr Ala
             115                 120                 125

Ile Phe Lys Met Ile Ser Pro Glu Asp Thr Lys His Leu Pro Glu Asp
     130                 135                 140

Glu Asn Thr Pro Glu Lys Arg Ala Glu Lys Ile Trp Gly Phe Phe Gly
145                 150                 155                 160

Lys Lys Asp Asp Asp Lys Leu Thr Glu Lys Glu Phe Ile Glu Gly Thr
                 165                 170                 175

Leu Ala Asn Lys Glu Ile Leu Arg Leu Ile Gln Phe Glu Pro Gln Lys
             180                 185                 190

Val Lys Glu Lys Leu Lys Glu Lys Lys Leu
         195                 200
```